United States Patent [19]

Cavendish et al.

[11] 3,949,428

[45] Apr. 13, 1976

[54] PROSTHETIC BONE JOINT DEVICES

[75] Inventors: Michael Edward Cavendish; John Thomas Matthew Wright, both of Merseyside, England

[73] Assignee: National Research Development Corporation, London, England

[22] Filed: Sept. 3, 1974

[21] Appl. No.: 502,961

[30] Foreign Application Priority Data

Sept. 7, 1973  United Kingdom............... 42303/73

[52] U.S. Cl.............. 3/1.911; 128/92 C; 128/92 E; 128/92 EB
[51] Int. Cl.² ........................................... A61F 1/24
[58] Field of Search.................... 3/1, 1.9–1.911; 128/92 C, 92 E, 92 EB

[56] References Cited
UNITED STATES PATENTS
3,837,009  9/1974  Walker................................ 3/1.911

OTHER PUBLICATIONS
The Polycentric-type Total Knee(Advertisement by Zimmer—USA), *The Journal of Bone & Joint Surgery*, Vol. 55-A, No. 3, Apr. 1973.
Original Gunston Polycentric Total Knee(Advertisement by Promed International Inc.), *The Journal of Bone & Joint Surgery*, Vol. 55-A, No. 3, Apr. 1973.
U.C.I. Total Knee, (Advertisement by Wright Mfg. Co.) *The Journal of Bone & Joint Surgery*, Vol. 55-A, No. 3, Apr. 1973.

*Primary Examiner*—Ronald L. Frinks
*Attorney, Agent, or Firm*—Cushman, Darby & Cushman

[57] ABSTRACT

An endoprosthetic knee joint device with separate pairs of femoral and tibial condylar runner and track components is improved in respect of bone cement fixation surfaces, mutually articulatory bearing surfaces, and securement location relative to each other and the relevant bones. The femoral components have L-shaped fixation surfaces defining a slightly obtuse angle, and the tibial component fixation surfaces are tapered. The femoral component bearing surfaces have longitudinal convex curvature of higher and lower order over respective end portions, the tibial component bearing surface has longitudinal concave curvature of lowest order, and these bearing surfaces have complementary lateral curvatures of highest order. All components have recesses at one end to engage a jig assembly which connects with the femur in predetermined relationship and locates the components relative to the natural condyles.

9 Claims, 8 Drawing Figures

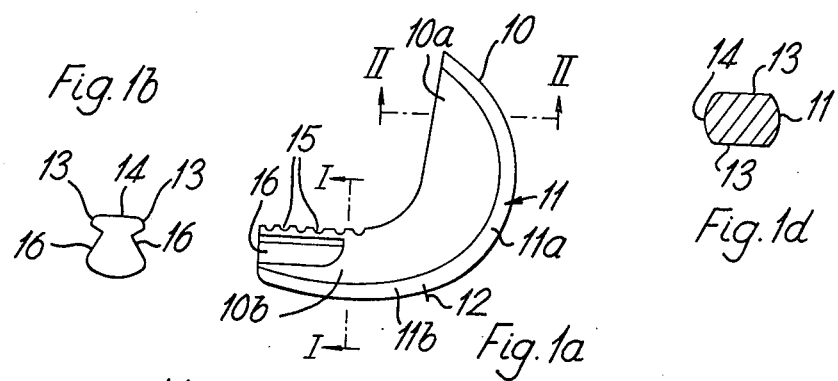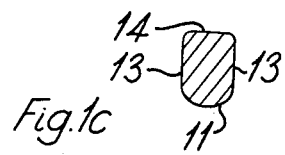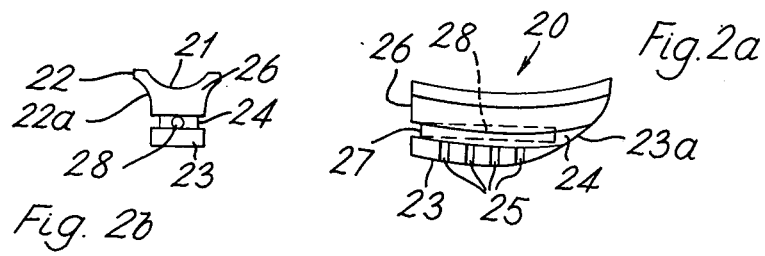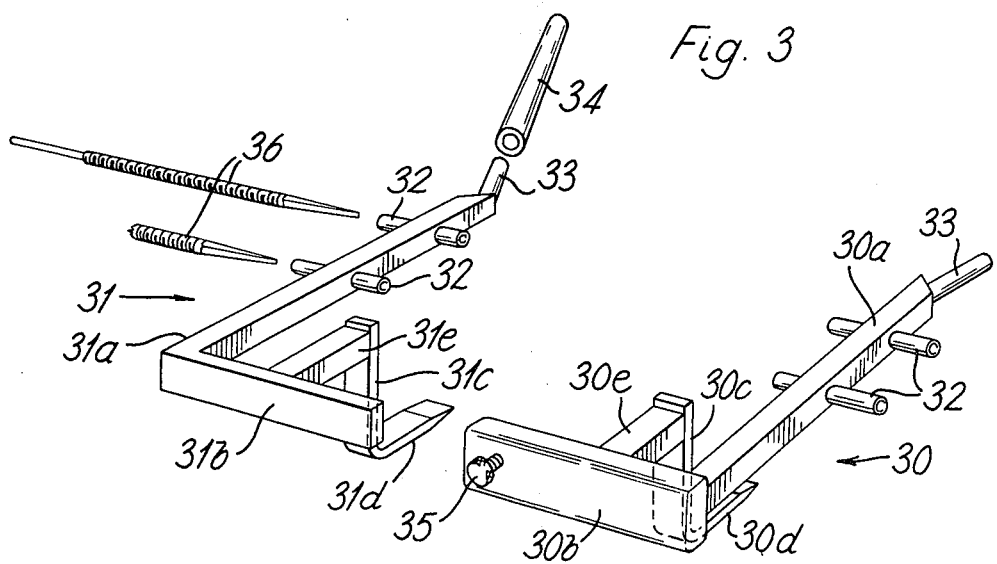

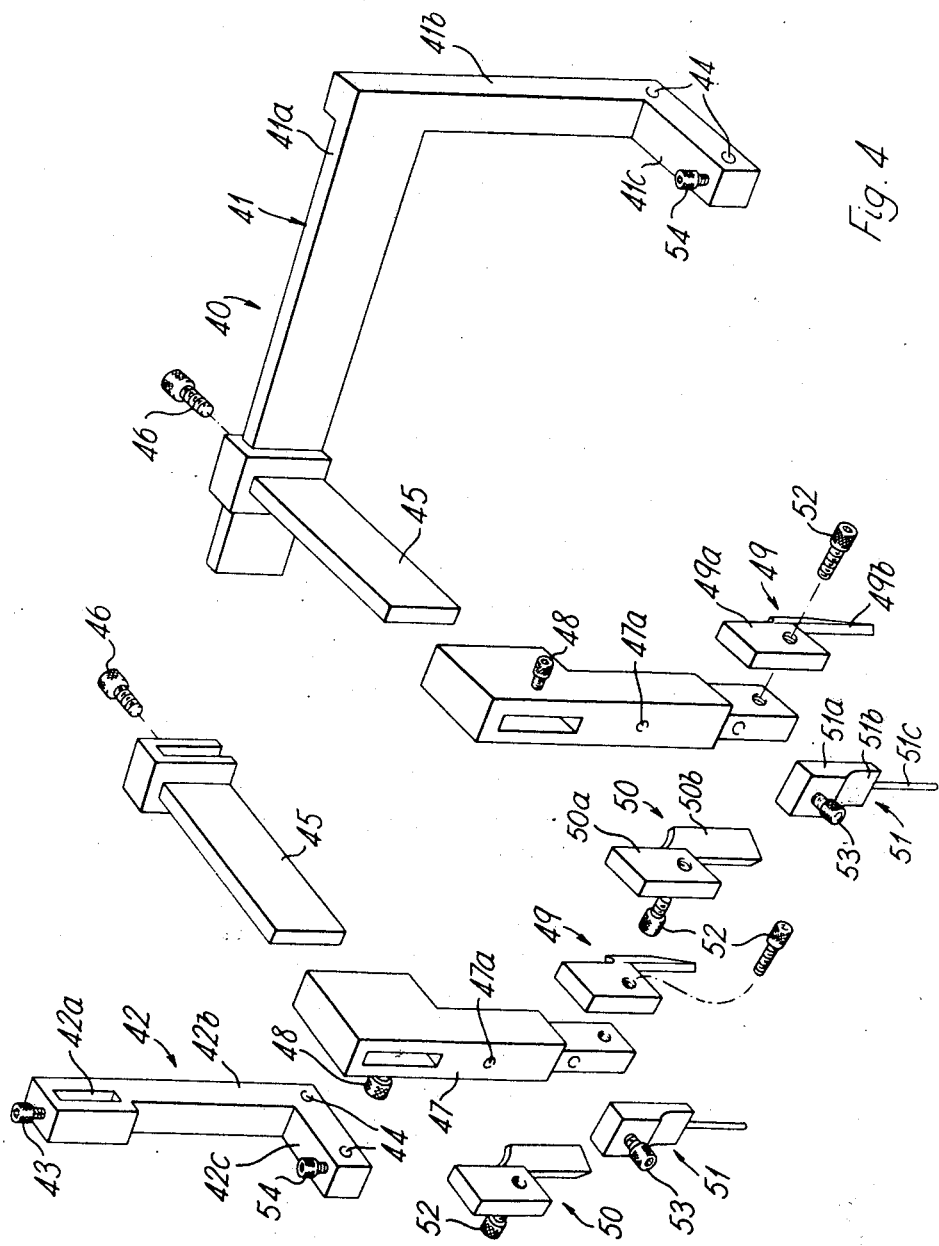

PROSTHETIC BONE JOINT DEVICES

This invention concerns prosthetic bone joint devices and, more particularly, endoprosthetic knee joint devices.

One form of such devices according to a more recent proposal (Gunston, "Polycentric Knee Arthroplasty," Journal of Bone & Joint Surgery, May, 1971) involves the provision of a pair of femoral runners having convex part-toroidal bearing surfaces for mutual articulatory bearing engagement in similar, but concave and longitudinally shorter, bearing surfaces in a pair of tibial component tracks.

The present invention provides improvements in this form of device and also improved means for use in the implantation of such devices.

The devices in question are normally secured with bone cement and one aspect of the present improvements concerns the fixation surfaces of the components which interface with this cement. For example, advantage is found to arise with use of a substantially L-shaped fixation surface for the femoral component extending longitudinally behind the respective convex bearing surface. This shaping serves to reduce the effect of forces which can otherwise tend to expel the component. More particularly, it is preferred that this shape defines a slightly obtuse included angle of about 95° which assists in extruding the cement in a desired manner. A similar extrusion effect is also obtained by convergently tapering the fixation surface of each tibial component.

Another aspect of the invention concerns the bearing surface of the components. The femoral components are preferably formed with bearing surfaces having higher and lower order longitudinal curvatures over opposite end portions thereof, and the tibial component bearing surfaces with longitudinal curvatures of lowest order to better simulate the natural joint geometry and function. At the same time these bearing surfaces preferably have complementary lateral curvatures of highest order, and all of these curvatures are conveniently of circular form.

A remaining aspect of the invention concerns facilitation of accurate implantation. To this end the components are preferably formed with recesses at corresponding ends for engagement with a jig assembly which is connectable to the femur in a predetermined relationship and serves to locate the components in a predetermined spatial relationship.

For a clearer and fuller understanding of these and other aspects of the invention, the same will now be described, by way of example, with reference to the accompanying drawings, in which:

FIG. 1 is a multi-part illustration of a femoral component for use in the invention in which illustration a is a side elevation, b is a part end elevation of a, and c and d are cross-sectional views respectively taken at I—I and II—II in a;

FIG. 2 similarly illustrates a tibial component in a side elevation, and b a part end elevation; and FIGS. 3 and 4 are similar exploded perspective views of a jig assembly embodiment for use in implantation of the illustrated prosthesis components.

The illustrated femoral component is one of two identical components employed in a presently preferred embodiment of the invention, and it is appropriate therefore to describe only one of these components. The same is true of the illustrated tibial component, which forms part of the same embodiment, and also of some of the components of the illustrated jig assembly which is of a presently preferred form for use in implantation of the relevant prosthesis embodiment.

Considering then the femoral component of FIG. 1: this is denoted at 10 and takes the form of a generally L-shaped elongated member. The outermost surface of this member remote from the included angle of the L-shaping is convexly curved both longitudinally and laterally to define a bearing surface 11 whereby the member serves as a runner. The longitudinal curvature of the surface 11 is not uniform, but of a higher order over one end portion 11a extending over one arm 10a of the member 10, and a lower order over the other end portion 11b extending over the other arm 10b. In this particular instance these two longitudinal curvatures are each circular and merge smoothly at their junction 12 where they have common tangents. The lateral curvature of the surface 11 is uniform, and in this instance circular and of significantly higher order than the longitudinal curvatures just mentioned.

The remaining two side faces, and the innermost face of the member 10, are denoted at 13, 13 and 14, respectively, and are generally flat apart from two features. The first of these features comprises a series of grooves 15 which each extend laterally wholly across the face 14 of the arm 10b, and which are mutually spaced longitudinally along the face 14. The second of these features comprises two like notch-form, jig-engageable recesses 16 respectively formed in the faces 13. These notches are of V-shape and extend longitudinally partway along the arm b from the free end of the latter.

A further feature of the member 10 is that the included angle thereof is obtuse, this angle being a little greater than a right angle and, in this instance, 95°.

Lastly regarding the structure of the member 10: it is preferably made of metal and, in this instance, is of a suitable grade of stainless steel.

The illustrated tibial component is denoted at 20 and also takes the form of an elongate member, but is of generally slightly curved form rather than angled. Considering the member 20 as if formed from a curved bar of rectangular cross-section: the innermost surface is concavely relieved to provide a bearing surface 21 whereby the member serves as a track for co-operation with the illustrated femoral component runner member 10 as will be clearer hereinafter. The longitudinal curvature of the surface 21 is uniformly circular and of a lower order than that of either portion of the corresponding femoral component surface 11. The lateral curvature of the surface 21 is also uniformly circular and is substantially the same as that of the surface 11. It is, in addition, to be noted that the longitudinal extent of the surface 21 is significantly less than that of the surface 11, while the lateral extent of the former exceeds that of the latter.

The remaining long faces of the member 20 are the two side faces denoted generally at 22, and the outer face denoted similarly at 23. The faces 22 are relieved at 22a to reduce the width of the member 20 below the depth to which the surface 21 penetrates, and these relieved face portions 22a are themselves each provided with a longitudinal groove 24. The face portions 22a are also grooved by the provision of a series of grooves 25 which each extend laterally from the outer longitudinal periphery to the respective longitudinal groove 24. One end portion 23a of the face 23 is inclined towards the bearing surface 21 to provide the member 20 with a partly tapered form.

The end face 26 of the member 20 which is remote from this tapering is grooved at 27 to communicate the grooves 24, and the member is provided with a jig-engageable recess in the form of a longitudinal bore 28 which communicates at one end with the groove 27.

Lastly regarding the structure of the member 20: it is preferably made of plastics material and, in this instance, is of high density polyethylene.

In use of the illustrated components just described, the femoral and tibial components are secured with the use of acrylic cement or equivalent gap-filling medium in respective slots formed in the femoral and tibial condyles. More specifically, each femoral component is located with its arms 10a and 10b respectively extending along the posterior and anterior portions of the relevant femoral condyle, the tibial components are located in the superior portions of the tibial condyles, and the components are all mutually parallel with corresponding femoral and tibial components in mutually facing disposition so that their bearing surfaces are engaged. This engagement is such that, in a position of maximum extension, the bearing surface portion 11b engages the associated surface 21 with their corresponding free ends substantially aligned, and the surfaces mutually slide and roll to engage surface portion 11a with surface 21 with increasing flexion. This engagement is maintained and controlled by retention of the natural ligaments of the joint and the situation is basically similar to that which arises with the prior prosthetic devices discussed in the foregoing introduction. However, there are some important differences.

One such difference arises in connection with the longitudinal curvature of the femoral components. In the natural joint this curvature is not uniform but is likened to that of a spiral — more specifically a cardioid — having increasing curvature from its inferior to posterior portions. This feature of the joint is a factor, together with ligament action, in constraining the articulatory capability and enhancing the stability of the knee with increasing flexion towards a fully extended configuration. The presently proposed device simulates this situation by the provision of similarly varying longitudinal curvature for the bearing surfaces of the femoral components, and in the illustrated embodiment this involves the use of two circular curvatures to facilitate manufacture. Thus, as in the natural joint, the effective radius of curvature increases with articulation towards full extension to enhance stability by tensing the ligaments and to constrain articulation capability by reducing that for rotation about the long direction of the leg. Also, as in the natural joint, the present device involves an increase in the area of bearing surface engagement with increasing flexion towards full extension.

In contrast to these similarities between the natural joint and present device, the prior devices involve uniform longitudinal curvatures for both of the femoral and tibial components which cannot by themselves vary the prosthesis stability in any of the above ways.

Another difference in the illustrated device arises with the L-shaping of the femoral components. One of the arms of this shaping is secured orthogonally to the long axis of the leg to assume the role of a natural condyle inferior portion, and is accordingly orthogonally disposed relative to the line of action of the maximum load forces applied through the devices. Such forces occur in the direction of the long axis of the leg with the knee joint fully extended and in the present instance will have a minimized tendency to loosen the device. In the prior devices, on the other hand, use is made of femoral components having solid semi-circular disc form and the diametral face of this form is located in an inclined disposition relative to the long axis of the leg. This disposition is such that the aforementioned maximum load forces apply a wedge action tending to expel the femoral components.

A further difference in the illustrated device arises from the provision of inclined inner face portions on both components which act to enhance extrusion of cement during securement as will be appreciated hereinafter.

Considering now the associated jig assembly: this involves two sub-assemblies which are respectively illustrated by FIGS. 3 and 4.

The first sub-assembly comprises a pair of guide members 30 and 31 which are each of similar compounded L-shaping, but of mutually reflected geometry to serve as left and right hand members. This shaping of the guide members involves a main L-shape formed by first arms 30a and 31a and second arms 30b and 31b extending perpendicularly therefrom. A subsidiary L-shape is formed by third arms 30c and 31c, and fourth arms 30d and 31d; and fifth arms 30e and 31e serve to join the two L-shapes of each member. The fifth arms extend from locations partway along their respective second arms, in a similar sense and parallel to their respective first arms. The third arms join their fifth arms remotely from their second arms, and extend mutually orthogonally with their first, second and fifth arms. The fourth arms join their third arms remotely from their second arms, and extend in a similar sense and parallel to their first arms.

Each first arm has a pair of tubes 32 passing therethrough parallel with the respective second arm, and at its free end each first arm has a stem 33 extending therefrom in inclined manner. Each stem 33 lies in the plane of its first and second arms, and is inclined by about 15° away from the second arm. Also, each such stem can be extended by location of a handle 34 thereon.

Lastly regarding this sub-assembly structure, it is to be noted that the second arms are longitudinally slidably engageable one within the other at their free ends, and can be secured by a screw 35 when so engaged. This engagement aligns the pairs of tubes 32.

In use of this first sub-assembly, the knee joint is suitably exposed, the leg is flexed at the knee, and the first arms are located along opposite sides of the femoral portion of the leg with the second arms extending laterally across the region of the femoral condyles in adjustable engagement to locate the third and fourth arms in engagement with respective inferior and posterior portions of the femoral condyles. This location can be facilitated by use of the handle 34 to extend the stem 33 of the laterally outermost first arm.

When so located, the screw 35 is tightened and the tubes 32 employed as drill guides to pass a pair of Steinman pins 36 through the femur. This pinning securely locates the sub-assembly in a predetermined location relative to the femoral condyles, and these condyles are then each sawed in the plane of the respective subsidiary L-shape by guiding the saw along both sides of the relevant third and fourth arms. The first sub-assembly is then removed except for the pins 36, the femoral condyles slotted by removal of the bone between the relevant saw cuts, and the tibial condyles similarly slotted after sawing with the knee fully extended to employ the femoral slots as saw guides.

Use is then made of the second sub-assembly which comprises a frame 40 made up by two parts 41 and 42. The part 41 involves an elongated member of which three successive lengths 41a, 41b, 41c extend in mutually orthogonal manner. The member 42 has lengths 42b and 42c which correspond to 41b and 41c, with the free end of length 42b being apertured at 42a to receive the free end of 41a in sliding engagement securable by a screw 43. This engagement produces a bridge-like structure of which 41a is the span, 41b and 42b are legs, and 41c and 42c are feet. The lengths 41c and 42c each have a corresponding pair of parallel bores 44 therethrough, which bores are aligned when the parts 41, 42 are engaged.

The frame is associated with a pair of like arms 45 which are individually slidably engageable on the frame length 41a to extend in spaced side-by-side manner parallel to the frame lengths 41c, 42c, and the arms 45 can be individually secured to the frame by screws 46.

Similarly, the arms 45 are respectively associated with a pair of like arms 47 which are slidably engageable on the former to extend therefrom in spaced side-by-side manner parallel to the frame lengths 41b, 42b. These further arms 47 can be individually secured by screws 48.

Each of the arms 47 is respectively associated with like prosthetic device component holders, each of which holders is in three parts 49, 50, 51. Two of the parts 49, 50 of each holder serve to hold one of the illustrated femoral components 10 on one of the arms 47. For this purpose each holder part 49, 50 comprises a plate 49a, 50a for connection by a screw 52 to a respective side of the free end of the relevant arm 47, and a jaw 49b, 50b which then extends longitudinally from the arm. These jaws serve to engage the notches 16 of the component 10. The remaining holder parts 51 each comprise a bar 51a for connection by a screw 53 to the outer face of the free end of the relevant arm 47, which bar is relieved at one end to provide a rib 51b from which a rod 51c projects longitudinally from the arm. The rib 51b and rod 51c serve to engage the groove 27 and bore 28 of a tibial movement.

In use of this second sub-assembly the members 41 and 42 of the frame 40 are engaged one with another and also, by way of their bores 44, with the ends of the pins projecting from the femur. Securement of the screw 43 then affords a rigid frame structure held in fixed relationship with the lower end of the femur, and this rigidity can be enhanced by the provision of further screws 54 to secure the parts 41c and 42c with the pins 36. The arms 45 are then engaged with the frame, the arms 47 with the arms 45, and the holders 49 and 50 to the arms 47 to grip dummy femoral components of similar form to those of FIG. 1. The sub-assembly is adjusted by way of its arms to locate the dummy components in the femoral slots, and then rendered rigid by tightening the various screws.

Thereafter the tibial components are located and cemented in their slots, the positioning of these components being verified with reference to the dummy femoral components held by the second sub-assembly. This procedure can be facilitated by use of a third sub-assembly (not shown) serving as a supplementary tibial component holding jig. Such a third sub-assembly involves a U-shaped structure of which the U-arm spacing is adjustable, and in which the U-arms terminate in holders similar to those denoted at 51 in FIG. 4, or separably receive the holders 51 themselves. In any event, the adjustment of the U-arms is set by plugging the pins of their holders in holes 47a in the arms 47 of the second sub-assembly, and the third sub-assembly is then used to carry the tibial components to their slots.

As a final step, the dummy femoral components and third sub-assembly are removed, and the femoral components located and cemented in their slots with use of the second sub-assembly and the component holders 49 to 51 to verify the positioning of these components with the femur and tibial components.

The advantages of this jig assembly are partly evident from the above description in that it affords accurate location of the components of the prosthesis in a predetermined relationship with each other and the bones to which they are to be secured. Moreover, this location is effected in a manner which does not require a high order of visual judgement on the part of the surgeon since the accuracy derives from the initial location of the first sub-assembly in a tactile manner with reference to relatively invariate geometry of the femur itself. A consequence of this situation is that there is no need to maintain the implantation site free of blood throughout the procedure as is normally the case by use of a tourniquet, and in this instance such a need only arises when cementing the components in their slots to allow removal of blood from the bone/cement interfaces. This results in a significant reduction of the duration of tourniquet application and enhances the subsequent recovery of the joint.

The jig assembly is also advantageous in allowing individually adjustable location of the components from the sides of the joint whereby there is no necessity to disconnect and displace the patella. Such displacement is a common feature in the implantation of all existing prosthesis which do not require permanent removal of the patella, and this is a factor which normally delays recovery.

A further advantage of the illustrated assembly arises from the bridge form of the frame, which form is readily gripped to facilitate separation of the femur and tibia.

While the invention has been described with more particular reference to the illustrated embodiments, it will be appreciated that it is capable of variation within the broader aspects thereof discussed initially. Indeed, these aspects themselves are capable of variation. The advantageous geometry of the prosthesis is applicable to a device having single femoral and tibial components for conditions where retention of the cruciate ligaments, and possibly the patella also, is not viable. Similarly the jig assembly is applicable to such a modified device, and is, in any case, not intended exclusively for use with prosthetic joint devices according to the present proposals.

We claim:
1. An endoprosthetic knee joint device, comprising:
   at least one femoral component of elongated overall form having a longitudinally curved convex bearing surface extending therealong, and a fixation surface wholly of substantially L-shape with first and second L-arms longitudinally coextensive with and transversely opposed to different end portions of said convex bearing surface;

and at least one tibial component of elongate form, but lesser longitudinal extent that said femoral component, having a longitudinally curved concave bearing surface in articulatory engagement with said convex bearing surface, and a longitudinally convergently tapered fixation surface extending therealong remotely from said concave bearing surface.

2. A device according to claim 1 wherein said L-arms are mutually inclined at an obtuse angle of about 95°.

3. A device according to claim 1 wherein said convex surface has longitudinal curvature of respectively higher and lower orders over different end portions thereof opposite said first and second L-arms, said concave surface has longitudinal curvature of lowest order, and said convex and concave bearing surfaces have lateral curvatures of highest order.

4. A device according to claim 1 wherein said femoral component is formed with mutually-opposed recesses extending longitudinally between one of said fixation surface L-arms and the adjacent end portion of said convex bearing surface, and said tibial component is longitudinally bored in its end remote from the narrowed portion of said tapered fixation surface.

5. An endoprosthetic knee joint device, comprising:
at least one femoral component of elongate form having a convex bearing surface extending therealong with longitudinal circular curvatures of respectively higher and lower orders over different end portions thereof, and a lateral circular curvature of highest order;
and at least one tibial component of elongate form, but lesser longitudinal extent than said femoral component, having a concave bearing surface extending therealong with a longitudinal circular curvature of lowest order, and a lateral circular curvature of said highest order;
wherein said femoral component is formed with mutually-opposed recesses extending longitudinally adjacent respective side edges of said convex bearing surface end portion of lower order longitudinal curvature, and said tibial component is longitudinally bored from one end thereof.

6. A device according to claim 5 wherein said femoral component has a substantially L-shaped fixation surface extending therealong with first and second L-arms respectively opposed to said convex bearing surface different end portions relative to the cross-sectional shape of said femoral component.

7. In combination:
an endoprosthetic knee joint device comprising;
a pair of like femoral components, each of elongate form having a longitudinally curved convex bearing surface extending therealong, each having a first fixation surface adapted for securement to a respective femoral condyle with bone cement, said first fixation surface extending longitudinally along said femoral component remotely from said convex bearing surface, and each having at least one first recess extending longitudinally in said femoral component from one end thereof between said convex bearing surface and said first fixation surface;
and a pair of like tibial components, each having a bearing surface in mutual articulatory engagement with a respective one of said convex bearing surfaces;
each having a second fixation surface remote from the respective engaged bearing surface and adapted for securement to a respective tibial condyle with bone cement;
and each having a second recess extending longitudinally in said tibial component from the end thereof adjacent said femoral component one end and between said tibial component bearing surface and second fixation surface;
and a jig assembly for location of said components relative to the femur and tibia, which assembly comprises;
a frame portion in the form of a bridge;
means for securing said frame portion to transversely span the femur in substantially predetermined relationship therewith;
a pair of first arms each laterally adjustably connected to said frame in mutually spaced side-by-side manner generally longitudinally of the femur;
a pair of second arms respectively longitudinally adjustably connected to said first arms to extend laterally therefrom in mutually spaced side-by-side manner inwardly of the femur towards the femoral condyles;
and a plurality of first and second component holders connected to and extending longitudinally from said second arms, said holders being respectively engaged with said first and second recesses to hold said femoral and tibial components in predetermined spatial relationship.

8. A device according to claim 7 wherein each of said femoral components has a pair of said first recesses in the form of mutually opposed grooves extending partway therealong, and each of said first holders comprises a pair of clamp jaws respectively engaged in said grooves.

9. A device according to claim 8 wherein each of said tibial components has said second recess in the form of a bore with a slot extending transversely across the bore mouth, and each of said second holders comprises a bar formation with a rod extending therefrom respectively engaged in said slot and bore.

* * * * *